United States Patent [19]

Ulich

[11] Patent Number: 4,963,024

[45] Date of Patent: Oct. 16, 1990

[54] METHOD AND APPARATUS FOR DETERMINING K FACTOR

[75] Inventor: Bobby L. Ulich, Tuscon, Ariz.

[73] Assignee: Kaman Aerospace Corporation, Bloomfield, Conn.

[21] Appl. No.: 216,087

[22] Filed: Jul. 7, 1988

[51] Int. Cl.⁵ ............................................. G01N 21/49
[52] U.S. Cl. .................................... 356/342; 250/574; 356/5; 358/228
[58] Field of Search .................... 356/5, 342; 250/574; 358/228

[56] References Cited

U.S. PATENT DOCUMENTS

| | | | |
|---|---|---|---|
| 2,541,374 | 2/1951 | Morton . | |
| 3,426,207 | 2/1969 | Fried et al. . | |
| 3,446,555 | 5/1969 | Kakn | 356/5 |
| 3,467,773 | 9/1969 | Heckman, Jr. . | |
| 3,566,021 | 2/1971 | Jakes, Jr. | 350/3.5 X |
| 3,670,098 | 6/1972 | Korpel | 350/5.3 X |
| 3,743,418 | 7/1973 | Heflinger | 356/5 |
| 3,782,824 | 1/1974 | Stoliar et al. | 356/342 |
| 3,902,803 | 9/1975 | Lego, Jr. | 356/5 |
| 4,030,831 | 6/1977 | Gowrinathan . | |
| 4,174,524 | 11/1979 | Moran | 358/95 |
| 4,197,088 | 4/1980 | Meserol et al. | 250/574 |
| 4,754,151 | 6/1988 | Billard | 356/342 X |

Primary Examiner—Vincent P. McGraw
Attorney, Agent, or Firm—Fishman, Dionne & Cantor

[57] ABSTRACT

A system is presented for the remote detection of the diffuse attenuation coefficient or K factor over very large areas and over relatively short time periods; and for determining depth in a body of water or other medium. In accordance with the present invention, a laser is used to generate short pulses of light with pulse widths on the order of nanoseconds. The laser light is expanded by optics and projected into the water or other medium. An intensified CCD (charge coupled device) camera is electronically shuttered after an appropriate time delay such that the image formed by the camera is composed of light backscattered by the water from a layer of range z and a thickness of $\Delta z$. The signal detected by the camera is $S_i$. If several measurements of $S_i$ are made at known time delay differences such that the differences of range gates $z_i$ are also known, then K can be calculated. The same apparatus can also be used to determine depth by measuring the time delay between the reflection from the surface of the medium and the reflection from the bottom of the medium.

25 Claims, 3 Drawing Sheets

METHOD AND APPARATUS FOR DETERMINING K FACTOR

BACKGROUND OF THE INVENTION

This invention relates generally to a method and apparatus for remotely determining the optical clarity or transmissivity of water and other mediums; and for remotely determining depth of water and other mediums. More particularly, this invention relates to a novel system for determining the diffuse attenuation coefficient or K factor for large areas of water and other mediums from a remote location and over a short period of time; and for remotely determining depth in water and other mediums over large areas and short periods of time.

The clarity or transmissivity of water is, in part, dependent on a factor known as K which is the diffuse attenuation coefficient. Thus, the determination of the K factor for a body of water will, in turn, provide information on water clarity. It will be appreciated that knowledge of water clarity (and K factor) is quite important for a variety of scientific, environmental and military applications. For example, information on sea water clarity is important to both Oceanographers and naval forces. Oceanographers are interested in determining the optical transmissivity of sea water because this information is useful in determining the density of phytoplankton (organisms) and its effect on the entire food chain; and in determining the sunlight available to sea organisms for photosynthesis.

Similarly, naval forces are interested in mapping water clarity for several reasons. First, absorption of visible light seriously hampers laser communications systems which may operate between a submarine and another submarine, a surface ship, an airplane, or a satellite. Therefore the effectiveness of such a secure communications link depends critically on knowing the sea water optical properties around the globe. Second, the effectiveness of some nonacoustic antisubmarine warfare (ASW) detection systems depends critically on the water optical transmission properties. Therefore it is essential to have water clarity data to judge the utility of such ASW systems. This is important at shallow depths and also to determine the depth of the thermocline.

The K factor is also important in pollution monitoring. Pollutants dissolved in water or floating on the surface must be detected accurately and over a short time period. Moreover, if the discharge is still in progress, detection of K factor can be used to trace the pollution back to the primary source.

K factor can also be utilized in bathymetry for detecting the bottom of a relatively shallow lake, river or ocean. This is of interest to hydrologists who want to know, for example, the flow rates of rivers (where water depth is needed). Cartographers are also quite interested in mapping ocean depths near shorelines and harbors to provide safe navigational passages.

Unfortunately, there is presently no known method which determines K factor readings as well as water depths from a remote location (e.g. airborne) over wide areas with sufficient accuracy in very short time periods and in a very cost effective manner. Prior art methods for ascertaining K factor typically utilize wire line devices which are cumbersome and time consuming. Such wire line devices also are limited to ascertaining K in limited areas as opposed to large areas.

SUMMARY OF THE INVENTION

The above-discussed and other drawbacks and deficiencies of the prior art are overcome or alleviated by the novel system of the present invention for remote detection of K factor over very large areas and over relatively short time periods; and for determining depth. In accordance with the present invention, a laser is used to generate short pulses (e.g. about less than 10 nm) of light with pulse widths on the order of nanoseconds. The laser light is expanded by optics and projected down toward the surface of the water. An intensified CCD (charge coupled device) camera is electronically shuttered after an appropriate time delay such that the image formed by the camera is composed of light backscattered by the water from a layer of range z and a thickness of $\Delta z$. The signal detected by the camera is $S_i$. If several measurements of $S_i$ are made at known time delay differences such that the differences of range gates $z_i$ are also known, then K can be calculated. Depth is measured by determining the time delay z between the reflection from the surface of the medium (e.g. water) and the reflection from the bottom of the medium.

The ICCD camera should have many pixels which can be used to map K over a significant area in a rapid and efficient manner. Thus, local variations in K in x, y and z coordinates may be determined. Digital imaging processing by computer can be used to find how K varies with range or depth for each camera pixel.

The attenuation coefficient of a backscattering medium can be found by the method of the present invention, independant of the physical form of the medium. Thus, the medium may comprise water, steam, fog, smoke, ice, snow, aerosols, dust, etc. The only requirement is that the medium be partially transmitting to the light over a distance scale corresponding to several camera gate widths (greater than or equal to $2 \Delta z$).

The above-discussed and other features and advantages of the present invention will be appreciated and understood by those of ordinary skill in the art from the following detailed description and drawings.

BRIEF DESCRIPTION OF THE DRAWINGS

Referring now to the drawings, wherein like elements are numbered alike in the several FIGURES.

DESCRIPTION OF THE PREFERRED EMBODIMENT

Figure 1:
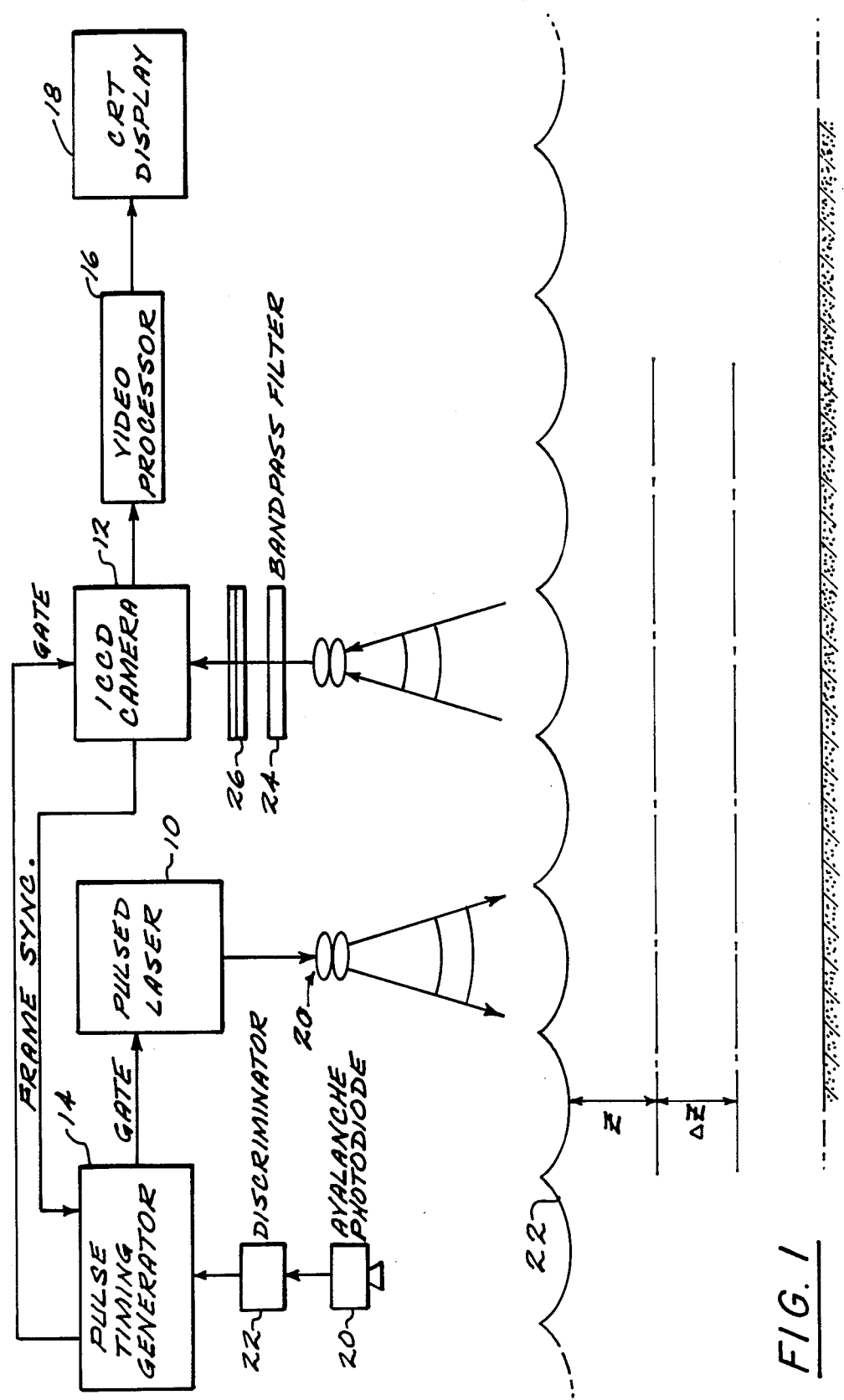
FIG. 1 is a schematic block diagram of the system for determining K-Factor in accordance with the present invention.

The present invention relates to a remote sensing unit for ascertaining diffuse attenuation coefficient or K-factor over a large area. This sensing unit also remotely ascertains depth in water and other mediums. Referring to FIG. 1, the present invention generally comprises a pulsed visible wavelength laser 10, a fast gated television camera 12, control electronics 14 for controlling laser 10 and camera 12, video processing unit 16 and CRT unit 18. When a light pulse is emitted from laser 10, the light is passed through a negative focal length lens 20 to expand the laser beam into a cone which illuminates a spot on the water surface 22. The shutter on camera 12 is opened briefly after an appropriate delay time such that the image formed by the camera and lens is composed of light backscattered by the water from a layer of depth or range z below the surface and a thickness of $\Delta z$.

The signals from the camera are then processed in video processing unit 16 to determine either K factor or depth and displayed on a CRT 18.

The diffuse attenuation coefficient of the backscattering medium at the laser wavelength is generally known as the K factor. The irradiance at a depth z below the surface is given by:

$$I(z) = I_o e^{-Kz} \quad (1)$$

where $I_o$ is the surface irradiance (in W/m²) of the light entering the water (which is assumed to cover a large area compared to the depth z).

The effective backscatter coefficient (reflectance) of the water layer is given by:

$$\frac{\sigma \pi}{2K} [1 - e^{-2K\Delta z}] e^{-Kz} \quad (2)$$

where $\sigma$ is the scattering coefficient at 180° relative to the angle of incidence.

At the water's surface, the effective radiance (in W/m²/sr) of the water layer is given by:

$$\frac{\sigma I_o}{2K} e^{-2Kz} [1 - e^{-2K\Delta z}] \quad (3)$$

where $I_o$ = source irradiance at water surface. Note that any surface reflection losses will be small and equal for all subsurface range gates (z).

Thus as a function of depth, the signal detected by the camera at range $z_i$ is:

$$S_i = \text{constant} \cdot e^{-2Kz_i} \quad (4)$$

where the constant depends on $\sigma$, $I_o$, K, and $\Delta z$ which are generally constant during a measurement at several values of the range gate depth $z_i$.

Suppose several (at least two) measurements of $S_i$ are made at known time delay differences such that the differences of the $z_i$'s are also known. In this case we can find K since $$\ln S_i = -2K z_i + c' \quad (5a)$$

$$\ln S_j = -2K z_j + c' \quad (5b)$$

where c' is a constant, $z_i$ is a measurement at a first range and $z_j$ is a measurement at a second range.

Subtracting (5b) from (5a) we get $$\ln S_i - \ln S_j = -2K(z_i - z_j) \quad (6)$$

$$\text{Thus } \ln(S_i/S_j) = -2K(z_i - z_j) \quad (7)$$

-continued $$\text{or } K = \frac{\ln(S_i/S_j)}{2(z_j - z_i)} \quad (8)$$

Of course, if K is assured to be a constant independent of depth z, averages of the (j−i+1) sets of intensity ratios and depth differences can be calculated. Alternatively, K can be computed for each pair of intensity measurements at its corresponding average depth ($\frac{1}{2}(z_i + z_j)$) so that variations of K with depth are apparent.

Bathymetry can also be performed by detecting the brighter signal return from the water surface glints and from the bottom of the body of water. The delay time between these two signals $\tau$ is related to the slant range depth z by:

$$z = \frac{c}{n} \tau \quad (9)$$

where c is the speed of light in a vacuum and n is the index of refraction of water at the laser wavelength. For example, for sea water at 532 nm, n=1.33 and c/2n=11.27 cm/ns. At 1 ns timing measurement accuracy, this corresponds to an approximate depth measurement accuracy of 11 cm.

The optical depth of the backscattering medium is $1/K$ or $K^{-1}$.

The attenuation coefficient (or optical depth) of a backscattering medium can be found by this method, independent of the physical form of the medium. It can be water, steam, fog, smoke, ice, snow, aerosols, dust, etc. The only requirement is that the medium be partially transmitting to the light over a distance scale corresponding to several camera gate widths ($\geq 2 \Delta z$). Thus, while the present invention has been described in conjunction with a body of water, the method and apparatus can equally be used with other backscattering mediums.

Absolute photometry is not required, but linearity of the photodetector is necessary. As shown in Equation (8), the ratio of two intensity signals must be measured with a narrow spectral filter in front of the camera; day and night operation can be performed equally well.

A television camera with many pixels can be used to map K over a significant area in a rapid and efficient manner. Thus local variations in K in x, y and z coordinates may be determined. This is useful in locating pollution sources (chemical or effluent discharges) in rivers, bays, oceans, etc. Digital image processing by computer can be used to find how K varies with range or depth for each camera pixel.

The present invention as depicted in FIG. 1 will now be described in much greater detail. It will be appreciated that the following description is of a preferred embodiment and that the particular component models, manufacturers and similar details are by example only.

Pulsed Laser

The preferred laser system used with the system of this invention is a Spectra Physics DCR-4 pulsed Nd:YAG laser which emits short pulses of infrared light at 1064 nm. The laser is operated in the green (532 nm) through the use of a Harmonic Generator which contains a frequency doubling crystal. The Harmonic Generator is externally mounted in front of the exit port of the laser cavity. The angle at which the initial laser pulse (1064 nm) strikes the crystal can be fine tuned so that the percentage of green light vs. IR that exits the Harmonic Generator can be varied. In general, the Harmonic Generator has an efficiency of approximately 50%, so the output power in the green is about half of the infrared input power.

Figure 3:
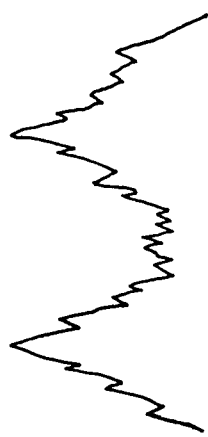
FIG. 3 is a diagram of a spatial profile of a single pulse from the laser of FIG. 2.
Figure 2:
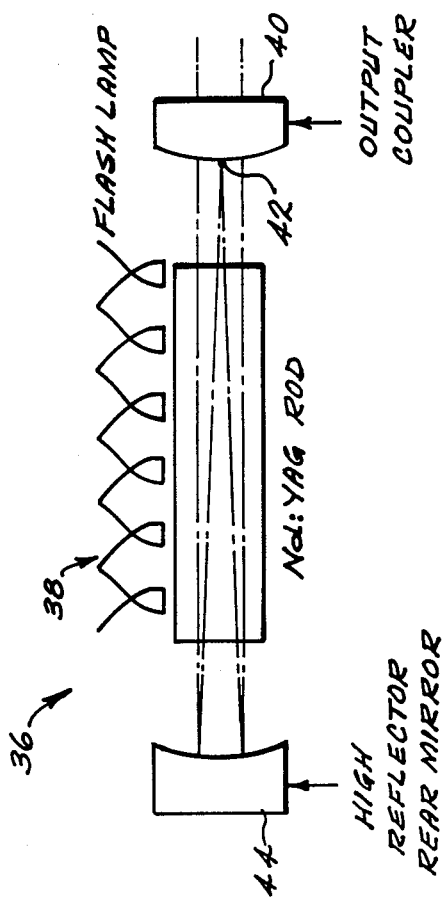
FIG. 2 is a schematic diagram of the pulsed laser used in the system of FIG. 1.

As shown in FIG. 2, the pulsed Nd:YAG laser uses a difraction-coupled resonator 36 which provides high energy, good stability, good beam quality, and a high degree of spatial coherence. The Nd:YAG rod is optically excited through the use of a high voltage flash lamp 38. The output coupler (front lens 40) has a single high reflectivity dot 42 located in the center of the convex subtrate. The rear mirror 44 is a concave high reflector which collimates the beam and will compensate for the thermal lensing of the Nd:YAG rod. The collimated beam passes through the rod on its exit path, and the light diffracts around the edge of the dot located on the front output coupler. This produces a characteristic "donut" spatial profile, as shown in FIG. 3. A Q-switch (Pockels cell) is used in conjunction with a Marx band and a quarter-wave plate to regulate the temporal width of the pulse. The initial storage of energy is accomplished by the quarter-wave plate. The light pulse is formed by applying a very high speed, high voltage waveform to the Pockels cell.

The preferred output specifications of the Nd:YAG laser being used for the system of this invention are:

| Pulse width at 532 nm | ≈3 ns |
|---|---|
| Pulse energy at 532 nm | ≈550 milijoules |
| Pulse repetition rate | 15 Hz |
| Output pulse jitter | <0.5 nsec from sync pulse |
| Total unit weight | ≈230 Kg |

The laser is externally cooled through the use of a self-contained cooling system. In addition, all cavities are air purged. The cooling system, electronics and purge system are housed in a separate power supply which is rack mountable. All cables, air and water lines are connected to the laser head and power supply by a 10 ft. umbilical cord. The laser can be operated at 208 V, 60 Hz, single phase power, or with 120/220 V power.

Cameras

Figure 4:
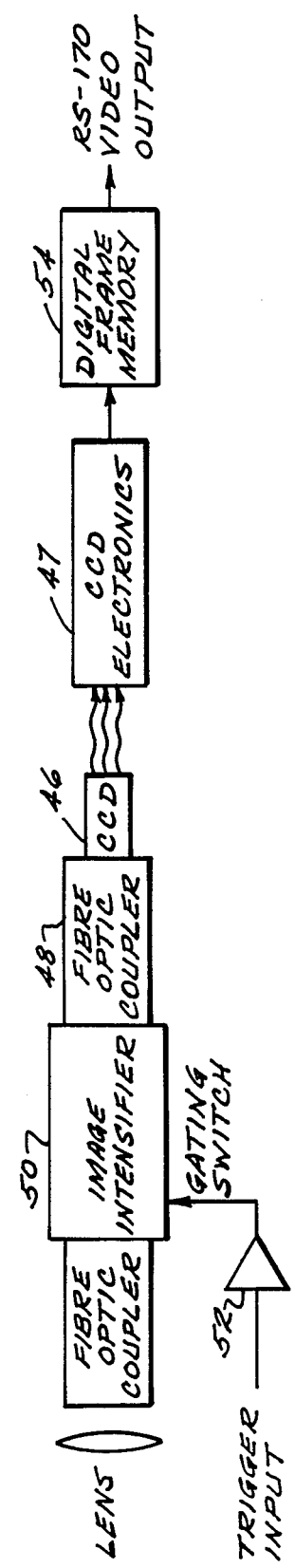
FIG. 4 is a schematic diagram of the CCD camera used in conjunction with the system of FIG. 1.

The preferred system of the present invention uses a Marco Scientific Model 201 Camera as shown in FIG. 4. The image sensor 46 used in this cameras is a Thompson CSF model TH-7882-FO charge coupled device (CCD) driven by CCD electronics package 47. This particular CCD features a fiber optic window 48 which is used to couple the sensor to an intensifier tube. The intensifier tube 50 serves as both a light amplifier and an ultrafast shutter driven by a high voltage amplifier 52. This camera also includes a built-in digital frame store/scan converter 54 whose output is converted to RS170 analog signal for display on a standard monitor 18 and for additional image processing.

The intensifier tube 50 is a DEP Model XX1420 with two gain stages. The first is a Gen II type intensifer with microchannel plate (MCP); the second is a Gen I proximity focused diode. Net luminance gain is nominally 100,000. The tube's S-20 photocathode defines the spectral response for the entire camera and establishes the quantum efficiency limitation at about 7%. The anode phosphor on the back end of the tube is fiber-optically coupled to the CCD sensor. A control switch on the camera body allows selection of an intensifier gate width of 10, 20 or 40 nsec. This is equivalent to an exposure setting for the camera.

The CCD being used is a novel frame transfer device. Normally in prior known RS170 compatible frame transfer devices, an image is integrated on the image area and then shifted to an adjacent storage area of the CCD. With each new TV line, the horizontal register shifts the stored information out. Since normal TV operates in an interlace mode, a phase shift between the odd and even field allows the CCD to operate in a kind of interlace readout mode. In these prior devices, the storage area occupies half the sensor and only half the elements actually integrate light. It is important to note that the sensor being used in the Model 201 Camera of this invention uses the entire area of the chip for light integration and, as such, is generally not compatible with standard RS170 operation. As will be discussed hereinafter, there are marked benefits of having a 100% sensitivity chip area in terms of ultimate system sensitivity.

The CCD features 568 lines by 382 columns of 23 micrometer square pixels in a contiguous format. Of this array, only a nominal 512 lines are used to achieve the correct aspect ratio for display on a standard video monitor (4:3 aspect ratio). Because of the desire for maximum signal-to-noise ratio and due to the limited requirement for spatial resolution, the Model 201 Camera takes advantage of pixel binning. The horizontal register shifts two charge packets into each charge detection stage before the stage is reasserted and four CCD lines are shifted to the horizontal shift register and summed before transfer. In this manner, the effective array becomes 128 lines by 191 columns of elements (bins) measuring 92 $\mu m \times 46$ $\mu m$. Each of these bins possesses the same readout noise limitation as a single pixel but collects $8\times$ the signal. Binning thus offers an improvement in SNR of about 2.8.

As previously stated, the CCD being used here is generally not compatible with standard RS170 video output. In the imaging lidar system of the present invention, the following sequence takes place to achieve a suitable video output:

(1) The CCD is undergoing continual downward shifting of the horizontal shift registers to clear away any dark current build-up.

(2) An external trigger signal turns on the intensifier to start an exposure. Upon receipt of this signal the CCD shift mode is interrupted and for the next 3.2 msec, the CCD is in the integration mode. The 3.2 msec allows the phosphor persistence to decay to less than 5% after the short (20–40 nsec) exposure, thus serving to optimize SNR.

(3) At the end of the 3.2 msec, the CCD is switched into the readout mode where the accumulated charge for each bin is read into the digital frame store. In addition to the digitizing of the data, a format manipulation occurs in the frame store in which the sensor image is effectively rotated 90 degrees (i.e., columns are converted to rows and vice-versa). The 3:4 aspect ratio of the sensor now maps properly onto the 4:3 aspect ratio of a standard video monitor. This entire process takes 8.2 msec.

(4) Once readout into the frame store is complete, the CCD reverts back to the continuous shift mode to eliminate dark current build-up until the next intensifier trigger is received.

A D/A converter outputs the frame store information as a composite video field. This field gets repeated at 60 Hz until the frame store is updated. Alternating fields in the composite video, although identical, get interlaced in the conventional manner. Each time the signal is received to begin an integration and readout on the sensor, a single blank field is generated on the composite video. Note that the total time for integration and readout (3.2+8.2 msec) is within a field interval (16.67 msec). It should be noted that the video field consists of 190 lines. After the 190 lines, the frame converter switches to a standard TV display mode and displays the remaining lines as black.

Several of the camera control features have already been mentioned. These include the external gating trigger via an input on the camera body and the gate width control switch (10, 20 or 40 nsec). Also found on the camera body are three outputs. The Gain Monitor shows a divided down replica of the high voltage gating pulse going to the intensifier tube. The Frame Synch out is a 1.98 μsec wide TTL negative pulse indicating the start of an odd field in the composite video, and thus occurring at 30 Hz. The Field Synch out is a 1.33 msec TTL negative pulse indicating the retrace blank (or vertical flyback) occurring between each field of the composite video at 60 Hz. A rack mountable power supply provides the low voltage power of the camera electronics as well as the high voltages needed for the two stages of the intensifier tube. There is potentiometer control for manual control of the high voltages on the power supply front panel. This is used to vary and monitor gain through the tube. In a preferred embodiment, an automatic gain control circuit is used to automatically correct gain at field rate.

Referring to FIG. 1, the timing control schematic for the system of this invention is shown. The principal elements in the overall timing scheme are the camera 12 and a Standard Research Model DG535 Digital Delay Generator 14. The 30 Hz Frame Synch signal from the camera is divided down to 15 Hz and used to trigger the laser (see FIG. 1). Recall that the Frame Synch signal occurs at the beginning of the odd field interval in the camera composite video. A laser output pulse is generated roughly 250 μsec after the trigger. The laser glint return from the water surface is detected by an Antel Optronics ARX - SA high speed avalanche photodetector 20. Given the expected altitude of the platform in an operational system, glint detection will generally be on the order of 1 μsec after laser pulse out. The photodetector signal is conditioned through a Modern Instrument Technology F-100T Pulse Pre-Amp and Noise Discriminator 22. The threshold of the F-100T is set above the noise level and along the linear region of the signal source. A 100 ns wide TTL pulse is output when the signal source reaches the threshold level. This TTL pulse triggers Stanford delay unit 14. This pulse timing generator 14 is the primary timing control for the system and is used to trigger intensifier gating for the CCD camera 12. It is set for a delay of (66 ⅔ ms — system delays + desired water depth delay). Hence, the camera is actually triggered on the previously detected glint pulse. System delays will be on the order of 130 ns (i.e. 40 ns propagation delay of the camera gate, 85 ns propagation delay of the Stanford, and <5 ns for other delays such as cable lengths, etc.). These delays can be accurately measured and should have jitter specifications <1 ns. The Stanford is capable of delaying a pulse very accurately for many millisec with its internal timebase oscillator. The RMS jitter specification is defined as: (50 ps + delay X 10E-8). For example, delays on the order of 70 ms have a RMS jitter spec of 0.7 ns. Once the system is calibrated, the delay is independent of distance from the water surface (i.e., the system automatically tracks changing platform altitude). However, this requires that the event be initiated accurately to within <2 ns at 15 Hz rep rate. This is possible only if the Frame Synch of the CCD camera is stable to <1 ns and the laser jitter referenced from TTL input is stable to <1 ns.

At the beginning of every other odd video field, an event is initiated (i.e., the laser is pulsed at 15 Hz). The laser return is detected and the round trip pulse transit time is taken into account in gating the cameras on at the desired time for a given water depth on the next event (laser pulse). This gating will always occur during the first several hundred μsec of alternating odd video field intervals. Then sensor integration and readout occurs for 3.2 μsec and 8.2 μsec, respectively. During this field interval when intensifier gating, sensor integration, and sensor readout occurs, an entire blank composite video field is read out of the camera's framestore. The ensuing three video fields are identical presentations of the captured event as read from the camera framestore. During this time, the camera waits for a trigger to initiate a new event and continually clears dark current from the CCD. The next trigger always occurs near the beginning of the fourth successive composite video field interval and the cycle is repeated.

Video Processor

A RS 170 signal from the intensified CCD camera is first patched through a monochrome video monitor (Kohu Model 9029B/2R) and is then fed into the inputs of the image processor. The image processor 13 is a computer which digitizes each pixel in the image and, based on the intensities measured as a function of range, computes the K-factor for each pixel and displays it as a monochrome intensity or as a colorized (false color) picture.

Camera Lens Optics

The system of this invention may optionally contain certain small optical filters including bandpass filters and polarizing filters. Two custom bandpass filters 24 can be used in the system. The first pair is mounted in a standard 52 mm photographic filter holder for use with the 25 mm f/0.85 Fujinon TV lenses. The field of view of these lenses are 20° half-field. The central wavelength and bandwidth of these filters are therefore made to be 537 nm and 11.8 nm respectively in order to make the transmission at 532 m as uniform as possible across the full field while minimizing the bandwidth. The second filter 24 is mounted in special filter mounts that are bonded to the 75 mm focal length f/1.0 Kowa lenses. The filters are 3.5" in diameter and 0.335" thick. The central wavelength and bandwidth of these filters are made to be 532.6 nm and 1.4 nm respectively in order to make the transmission at 532 nm as uniform as possible over the 7° half-field of the Kowa lenses.

A pair of polarizing filters 24 may also be employed to control sensitivity or to reduce glare.

Figure 6:
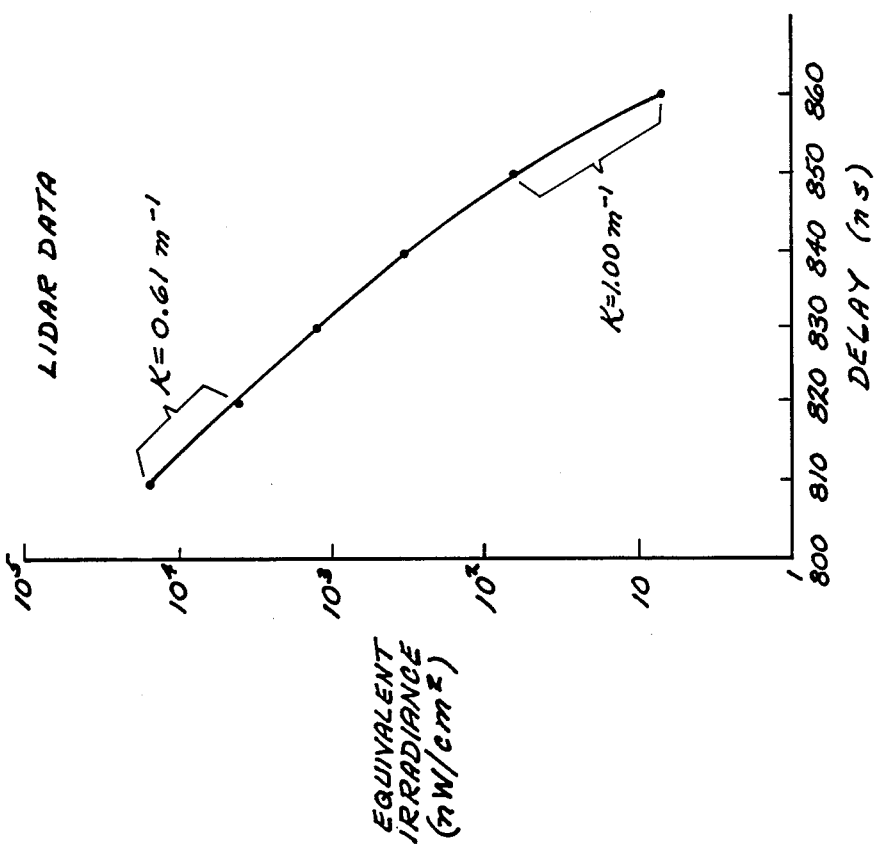
FIG. 6 is a graph of K developed by the system of FIG. 1.
Figure 5:
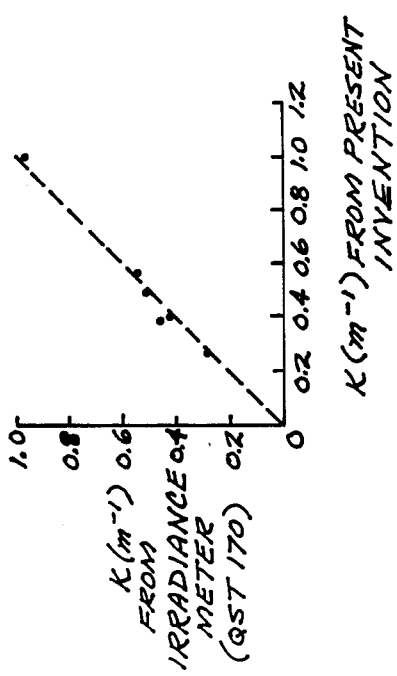
FIG. 5 is a graph comparing K derived from the present invention to K derived from a prior art K meter.

The method and apparatus of the present invention for detecting K factor has been successfully tested and excellent agreement has been found between the K values determined by this invention and those determined from measurements with a commercially available underwater irradiance radiometer (Biospherical Instruments Model QST-170). FIG. 5 reflects the excellent accuracy of the K-Meter of this invention inferred from the close agreement with in situ measurements of the dipping photometer. An example of data developed by the apparatus of this invention is shown in FIG. 6. The slope changes from $K=0.61$ $m^{-1}$ to $K=1.00$ $m^{-1}$ about 4 meters below the surface.

The method of the present invention can be used as a K-Meter (using equation 8) to ascertain water clarity and monitor pollution; and in bathymetry techniques (using equation 9). For example, oceanographers can utilize the present invention to determine the optical transmissivity of sea water to determine the density of photoplankton (organisms) and its effect on the entire food chain; and in determining the sunlight available to sea organisms for photosynthesis. Naval forces can also use the present invention for mapping water clarity which is important in maintaining laser communications networks and in certain nonacoustic antisubmarine warfare detection systems.

Pollutants dissolved in water or floating on the surface may also be detected using the imaging lidar K-Meter of this invention. By operating the system from an aircraft, pollutants can be detected and, if the discharge is still in progress the pollution can be followed back to the primary source. This can be done in the ocean or in fresh water lakes and rivers. Oil spills are easily detected and the extent of the spread of this pollution can be determined in an easier fashion than by measuring concentrations from water samples collected at regular grid points.

The present invention can also detect the bottom of a lake, river, or ocean if the water is reasonably shallow. By detecting both the surface glint and the bottom reflection, a water depth reading can be made for each pixel in the image. This is of interest to hydrologists who want to know, for instance, the flow rates of rivers. The flow rate is generally determined by multiplying the water velocity times the river cross-sectional area. Bathymetry is therefore useful since it determines the water depth as a function of horizontal position from which the cross-sectional area can be calculated. Similarly, Cartographers are quite interested in mapping ocean depths near shorelines and harbors to provide safe navigational passages.

Thus, an airborne imaging lidar as contemplated by this invention can give K-factor readings as well as water depths over wide areas with sufficient accuracy in very short time periods and in a very cost effective manner without the necessity for cumbersome and time consuming wire line devices.

While the present invention has been described using a single camera, an alternative method would be to utilize multiple cameras for measuring backscattered light intensity from multiple ranges by a single laser pulse thus increasing the speed in which K factor measurement can be made. Of course, a drawback to this alternative embodiment is the need for additional hardware (e.g. cameras).

While preferred embodiments have been shown and described, various modifications and substitutions may be made thereto without departing from the spirit and scope of the invention. Accordingly, it is to be understood that the present invention has been described by way of illustrations and not limitation.

What is claimed is:

1. A method of measuring the diffuse attenuation coefficient or K-factor in a backscattering medium which is at least partially transmitting to light including the steps of:
   selectively generating short pulses of light;
   projecting said short pulses of light toward the backscattering medium;
   detecting said pulses of light reflecting back from said medium after a time delay corresponding to the round-trip propagation time of said light pulses to and from said medium, said pulses of light being detected by at least one camera means, said camera means including automatic gain control means for automatically correcting gain at field rate; and
   converting said detected pulses of light to determine K-factor.

2. The method of claim 1 wherein:
   said short pulses of light are generated by pulsed laser means.

3. The method of claim 1 wherein:
   said short pulses comprise pulse widths of less than about 10 nanoseconds.

4. The method of claim 1 including:
   expanding said generated pulses of light by directing said pulses through optical means.

5. The method of claim 1 including:
   filtering said generated pulses of light.

6. The method of claim 5 including:
   using bandpass filter means to filter said pulses of light.

7. The method of claim 1 wherein:
   said pulses of light are detected by multiple camera means.

8. The method of claim 1 wherein:
   said camera means includes an intensified charge coupled device (CCD) sensor.

9. The method of claim 8 wherein said camera means further includes:
   fiber optic window means; and
   intensifier tube means, said fiber optic window means coupling said CCD sensor to said intensifier tube means to define said intensified CCD sensor.

10. The method of claim 1 including:
    displaying said detected pulses of light on cathode ray tube means.

11. The method of claim 1 wherein K-factor is determined by the equation:

$$K = \frac{\ln (S_i/S_j)}{2(z_j - z_i)}$$

where
   $z_i$ = measurement at a first range;
   $z_j$ = measurement at a second range;
   $S_i$ = signal detected at range $z_i$; and
   $S_j$ = signal detected at range $z_j$.

12. The method of claim 1 wherein said backscattering medium comprises water, the water including a surface, and including:
   detecting the leading edge of light reflected back from said surface of said water using glint detection means.

13. An apparatus for measuring the diffuse attenuation coefficient or K-factor in a backscattering medium which is at least partially transmitting to light comprising:

generating means for selectively generating short pulses of light;

projecting means for projecting said short pulses of light toward the backscattering medium;

at least one camera means for detecting said pulses of light reflected back from said medium after a time delay corresponding to the round-trip propagation time of said light pulses to and from said medium, said camera means including automatic gain control means for automatically correcting gain at field rate; and converting means for converting said detected pulses of light to determine K-factor.

14. The apparatus of claim 13 wherein:
said generating means comprises pulsed laser means.

15. The apparatus of claim 13 wherein:
said short pulses comprise pulse widths of less than about 10 nanoseconds.

16. The apparatus of claim 13 including:
means for expanding said generated pulses of light by directing said pulses through optical means.

17. The apparatus of claim 13 including:
means for filtering said generated pulses of light.

18. The apparatus of claim 17 wherein:
said filtering means comprises bandpass filter means.

19. The apparatus of claim 13 wherein:
said detecting means comprises multiple camera means.

20. The apparatus of claim 13 wherein:
said camera means includes an intensified charge coupled device (CCD) sensor.

21. The apparatus of claim 20 wherein said camera means further includes:
fiber optic window means; and
intensifier tube means, said fiber optic window means coupling said CCD sensor to said intensifier tube means to define said intensified CCD sensor.

22. The apparatus of claim 13 including:
means for displaying said detected pulses of light on cathode ray tube means.

23. The apparatus of claim 13 wherein:
said backscattering medium is water and wherein said pulses of light are projected toward a surface of the water.

24. The apparatus of claim 13 wherein K-factor is determined by the equation:

$$K = \frac{\ln (S_i/S_j)}{2(z_j - z_i)}$$

where
$z_i$ = measurement at a first range;
$z_j$ = measurement at a second range;
$S_i$ = signal detected at range $z_i$; and
$S_j$ = signal detected at range $z_j$.

25. The apparatus of claim 13 wherein said backscattering medium comprises water, the water including a surface, and including:
glint detection means for detecting the leading edge of light reflected back from said surface of said water.

* * * * *

UNITED STATES PATENT AND TRADEMARK OFFICE
CERTIFICATE OF CORRECTION

PATENT NO. : 4,963,024
DATED : October 16, 1990
INVENTOR(S) : Bobby L. Ulich

It is certified that error appears in the above-indentified patent and that said Letters Patent is hereby corrected as shown below:

Col. 2, Row 35: Delete "independant" and insert therefor --independent--.

Col. 3, Row 49: Delete " $S_i$=constant $\cdot$ e - 2K$z_i$ " and insert therefor -- $S_i$=constant $\cdot e^{-2Kz_i}$ --.

Col. 3, Row 57: Delete " ln $S_i$ - 2K $z_i$ + c$'$ " and insert therefor

-- ln $S_i$ = -2K $z_i$ + c$'$ --.

Col. 3, Row 59: Delete " ln $S_j$ - 2K $z_j$ + c$'$ " and insert therefor

-- ln $S_j$ = -2K $z_j$ + c$'$ --.

Col. 5, Row 49: Delete "cameras" and insert therefor --camera--.

Col. 8, Row 53: Delete "532 m" and insert therefor --532 nm--.

Col. 10, Row 58: Delete " $S_i$ = signal detected at range $z_j$ " and insert therefor -- $S_j$ = signal detected at range $z_j$ --.

UNITED STATES PATENT AND TRADEMARK OFFICE
CERTIFICATE OF CORRECTION

PATENT NO. : 4,963,024

DATED : October 16, 1990

INVENTOR(S) : Bobby L. Ulich

It is certified that error appears in the above-indentified patent and that said Letters Patent is hereby corrected as shown below:

Col. 12, Row 24: Delete " $S_i$ = signal detected at range $z_j$ " and insert therefor -- $S_j$ = signal detected at range $z_j$ --.

Signed and Sealed this

Fourth Day of January, 1994

Attest:

BRUCE LEHMAN

Attesting Officer

Commissioner of Patents and Trademarks